US009381511B2

(12) United States Patent
Daub et al.

(10) Patent No.: US 9,381,511 B2
(45) Date of Patent: Jul. 5, 2016

(54) MICROFLUIDIC SYSTEM AND METHOD FOR OPERATING SUCH A SYSTEM

(75) Inventors: Martina Daub, Weissach (DE); Juergen Steigert, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 1035 days.

(21) Appl. No.: 13/488,557

(22) Filed: Jun. 5, 2012

(65) Prior Publication Data

US 2012/0312380 A1 Dec. 13, 2012

(30) Foreign Application Priority Data

Jun. 7, 2011 (DE) ........................ 10 2011 077 101

(51) Int. Cl.

| | |
|---|---|
| ***G01N 21/00*** | (2006.01) |
| ***B01L 3/00*** | (2006.01) |
| ***A61J 1/06*** | (2006.01) |
| ***G01N 15/06*** | (2006.01) |
| ***G01N 33/00*** | (2006.01) |
| ***G01N 33/48*** | (2006.01) |

(52) U.S. Cl.

CPC ....... *B01L 3/50273* (2013.01); *B01L 3/502738* (2013.01); *B01L 2200/025* (2013.01); *B01L 2200/027* (2013.01); *B01L 2200/0621* (2013.01); *B01L 2300/0841* (2013.01); *B01L 2400/0644* (2013.01); *Y10T 137/0318* (2015.04); *Y10T 137/598* (2015.04)

(58) Field of Classification Search

CPC ....... G01N 15/06; G01N 33/00; G01N 33/48; G01N 21/00; B01L 3/00; A61J 1/06

USPC .......... 422/50, 68.1, 504, 503, 502, 521, 554; 436/43, 174, 180

See application file for complete search history.

(56) References Cited

U.S. PATENT DOCUMENTS

| | | | |
|---|---|---|---|
| 4,889,692 A | 12/1989 | Holtzman | |
| 5,573,951 A | 11/1996 | Gombrich et al. | |
| 6,096,276 A | 8/2000 | Laursen | |
| 2007/0099189 A1* | 5/2007 | Gomez-Elvira Rodriguez et al. | 435/6 |
| 2012/0107185 A1* | 5/2012 | Lebedev | 422/159 |
| 2012/0312380 A1* | 12/2012 | Daub et al. | 137/1 |

FOREIGN PATENT DOCUMENTS

| | | |
|---|---|---|
| DE | 10 2006 003 532 A1 | 7/2007 |
| WO | 02/20160 A1 | 3/2002 |

* cited by examiner

*Primary Examiner* — Brian J Sines

(74) *Attorney, Agent, or Firm* — Maginot, Moore & Beck LLP

(57) ABSTRACT

A microfluidic system comprises a cartridge that includes a first drum which has a first chamber and an adjustment device which is arranged so as to rotate the first drum about its mid-axis and is configured to connect the first chamber conductively to a second chamber. The microfluidic system further comprises a pressure device which acts upon at least one component with a pressure difference and is configured to transfer the component between the first chamber and second chamber.

14 Claims, 12 Drawing Sheets

MICROFLUIDIC SYSTEM AND METHOD FOR OPERATING SUCH A SYSTEM

This application claims priority under 35 U.S.C. §119 to patent application no. DE 10 2011 077 101.8, filed on Jun. 7, 2011 in Germany, the disclosure of which is incorporated herein by reference in its entirety.

BACKGROUND

The conduct of biochemical processes is based particularly on the handling of liquids. Typically, this handling is carried out manually with aids, such as pipettes, reaction vessels, active probe surfaces or laboratory equipment. These processes are sometimes even automated by means of pipetting robots or special appliances.

Microfluidic systems are sometimes also designated as what are known as lab-on-a-chip systems (pocket laboratory or chip laboratory) which accommodate the entire functionality of a macroscopic laboratory on a plastic substrate of only the size of a plastic card. Lab-on-a-chip systems are typically composed of two main components. A test carrier or a disposable cartridge contains structures and mechanisms for implementing the basic fluidic operations (for example, mixers) which may be composed of passive components, such as ducts, a reaction chamber, preceding reagents, or else active components, such as valves or pumps. The second main component comprises actuation, detection and control units. Such systems make it possible to carry out biochemical processes in a fully automated way.

Such a lab-on-a-chip system is described, for example, in publication DE 10 2006 003 532 A1. This system comprises a rotor chip which is provided so as to be rotatable with respect to a stator chip. The rotor chip can be coupled by means of fluidic ducts to the stator chip for the purpose of filling or emptying the rotor chip.

SUMMARY

The system and the method have the advantage, as compared with conventional solutions, that the cartridge does not have to be centrifuged in a centrifuge or exposed to another force field in order to transfer the component between the first and the second chamber. As compared with the use of a centrifuge, in a stationary system many parameters, such as, for example, the temperature of the component, can be set more simply. Furthermore, more flexible processing of the component is possible, since processing is independent of the rotational speed of the centrifuge.

Advantageous refinements of the disclosure may be gathered from the subclaims.

In the present context, "component" means a liquid, a gas or a particle.

In the present context, "chamber" preferably means a line portion, which is designed to be open on both sides or only on one side, or an essentially closed space which has an inflow and/or an outflow.

According to one refinement of the system according to the disclosure, the pressure device is designed as a pump and/or pressure accumulator, the pump and/or pressure accumulator preferably being connected by means of a pressure connection to the cartridge or being integrated into the cartridge. The necessary pressure can thereby be provided in a simple way in order to transfer the component between the first and the second chamber. Moreover, a highly compact set-up can be achieved by means of integration. The "pressure" may be an overpressure or an underpressure with respect to the ambient pressure.

According to one refinement of the system according to the disclosure, there is provision whereby the pressure accumulator stores the component itself under pressure and supplies it to the first or the second chamber or stores under pressure a fluidic aid which pressurizes the at least one component. The pressure accumulator is designed, in particular, as a gas cartridge, bubble store or spring accumulator. The aid is preferably a gas, in particular air, or water.

According to one refinement of the system according to the disclosure, the cartridge has a housing which is closed at one of its ends by means of an adapter, the adapter having the pressure connection. A plurality of functions are thereby integrated into the adaptor: to be precise, on the one hand, an especially sterile closure of the housing and, furthermore, incorporation of the pressure connection. Alternatively, the pressure connection may also be arranged at that end of the housing which lies opposite the adapter.

According to one refinement of the system according to the disclosure, the adjustment device comprises an electrically operated, mechanically operated and/or pressure-operated actuator which rotates the first drum and/or moves it along the mid-axis. The axial movement can therefore be provided in addition to the rotational movement and preferably takes place along the longitudinal axis of a housing of the cartridge.

According to one refinement of the system according to the disclosure, the actuator has a shaft which is connected directly or indirectly to the first drum in order to rotate the latter. The first drum can thereby be rotated, without the other drums having to be rotated.

According to one refinement of the system according to the disclosure, the adjustment device comprises a first slope which cooperates with a second slope of the first drum in order to bring the latter out of a first position, in which it is in positive engagement with a housing of the cartridge in a direction of rotation about the mid-axis, into a second position along the mid-axis, in which the positive connection is cancelled and the first drum rotates about the mid-axis by virtue of the action of a restoring means or of a further actuator. A type of "ballpoint pen mechanism" is thereby provided.

According to one refinement of the system according to the disclosure, the actuator actuates the first slope for cooperation with the second slope. That is to say, the actuator actuates the ballpoint pen mechanism.

According to one refinement of the system according to the disclosure, the first drum is preceded or followed by a second and/or a third drum with respect to the mid-axis, the actuator actuating the second and/or the third drum for the purpose of rotating the first drum. That is to say, the actuator acts directly upon the first drum in order to rotate this.

According to one refinement of the system according to the disclosure, the cartridge has a housing which is closed at one of its ends by means of an adapter, the actuator being fastened to the adapter. A plurality of functions are thereby integrated into the adapter: to be precise, on the one hand, an especially sterile closure of the housing and, furthermore, the accommodation of the adapter. The actuator is preferably integrated into the adapter.

According to one refinement of the system according to the disclosure, the adapter has a flexible diaphragm which can be actuated on one of its sides by means of the actuator and which acts on its other side upon the first, the second and/or the third drum. A sterile closure can thereby be provided. The actuator preferably lies outside the inner space of the housing.

According to one refinement of the system according to the disclosure, the second chamber precedes or follows the first drum with respect to the mid-axis and is formed in the second and/or the third drum. Since a plurality of drums, particularly with a plurality of chambers which are adjusted with respect to one another, are provided, the most diverse possible processes can be carried out automatically by means of the system.

According to a further refinement of the cartridge according to the disclosure, the second chamber and/or a third chamber precedes or follows the first drum with respect to the mid-axis, the first chamber preferably being conductively connectable selectively to the second chamber or to the third chamber by means of the adjustment device. The mixing chamber may therefore precede and/or follow the first drum or else be provided in the first drum itself. Moreover, the mixing chamber may preferably be connected selectively, as required, to different further chambers.

According to a further refinement of the cartridge according to the disclosure, a second drum, which has the second chamber, and/or a third drum, which has the third chamber, are/is provided. However, for example, the second drum may just as well also have the second chamber and the third chamber. The same applies to the third drum. Since a plurality of drums, particularly with a plurality of chambers which are adjusted with respect to one another, are provided, the most diverse possible processes can be carried out automatically by means of the cartridge.

According to one refinement of the system according to the disclosure, a plurality of second chambers are provided which can be acted upon by means of the pressure device with pressures different from one another, a respective second chamber preferably being connected by means of a respective pressure connection in the adapter to the pressure device, or all the second chambers being connected by means of a single pressure connection in the adapter to the pressure device, a respective second chamber more preferably being connected by means of a respective valve to the single pressure connection.

According to one refinement of the system according to the disclosure, the pressure device drives the actuator. Advantageously, therefore, only one energy source is required for the actuator and the pressure device.

BRIEF DESCRIPTION OF THE DRAWINGS

Exemplary embodiments of the disclosure are illustrated in the figures of the drawings and are explained in more detail in the following description.

In the drawing.

DETAILED DESCRIPTION

In the figures, the same reference symbols designate identical or functionally identical elements, unless specified otherwise.

Figure 1:
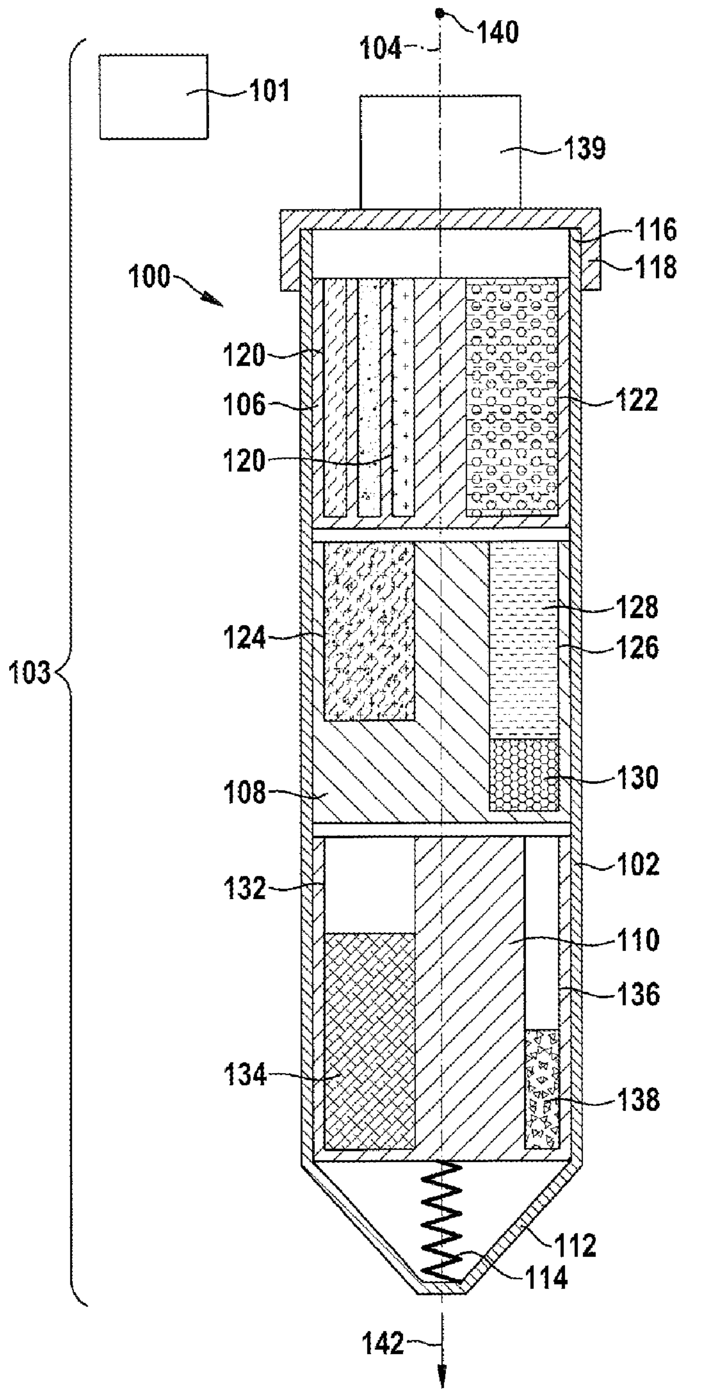
FIG. 1 shows a system according to an exemplary embodiment of the present disclosure, a cartridge of the system being illustrated in section and a pressure device being illustrated diagrammatically.

FIG. 1 shows a sectional view of a cartridge 100 and, diagrammatically, a pressure device 101 which together form a system 103 according to an exemplary embodiment of the present disclosure. The set-up of the cartridge 100 is first explained in more detail below in connection with FIGS. 1 to 4E.

The cartridge 100 comprises a housing 102 in the form of a small tube. For example, the housing 102 may be designed as a 5 to 100 ml, in particular 50 ml, centrifuge tube, 1.5 ml or 2 ml Eppendorf tube or, alternatively, a microtiter plate (for example, 20 μl per cavity). The longitudinal axis of the housing 102 is designated by 104.

The housing 102 accommodates, for example, a first drum 108, a second drum 106 and a third drum 110. The drums 106, 108, 110 are arranged one behind the other and with their respective mid-axes coaxially to the longitudinal axis 104.

The housing 102 is designed to be closed at one end 112. A restoring means, for example in the form of a spring 114, is arranged between the closed end 112 and the third drum 110 arranged adjacently to the latter. The spring 114 may be designed in the form of a helical spring or a polymer, in particular an elastomer. The other end 116 of the housing 102 is closed by means of a closure 118. The closure 118 can preferably be removed in order to extract the drums 106, 108, 110 from the housing 102. Alternatively, the housing 102 itself may also be disassemblable, in order to extract the drums 106, 108, 110 or to reach the chambers, for example the chamber 136.

According to a further exemplary embodiment, the spring 114 is arranged between the closure 118 and the second drum 106, so that the spring 114 is stretched in order to generate a restoring force. Other arrangements of the spring 114 may also be envisaged.

A respective drum 106, 108, 110 may have one or more chambers:

Thus, for example, the second drum 106 comprises a plurality of chambers 120 for reagents and also a further chamber 122 for accommodating a sample, for example a blood sample, which has been taken from a patient.

The first drum 108 following the second drum 106 comprises a mixing chamber 124 in which the reagents from the chambers 120 are mixed with the sample from the chamber 122. Moreover, the second drum 108 comprises, for example, a further chamber 126 in which the mixture 128 from the mixing chamber 124 flows through a solid phase 130. The solid phase 130 may be a gel column, a silica matrix or a filter.

The third drum 110 which in turn follows the first drum 108 comprises a chamber 132 for accommodating a waste product 134 from the chamber 126. Furthermore, the third drum 110 comprises a further chamber 136 for accommodating the desired final product 138.

The aim, then, is to control various processes within the cartridge 100 by means of an actuator 139. Thus, for example, the mixing chamber 124 is first to be connected fluidically to the chamber 122 in order to accommodate the sample from the chamber 122. The mixing chamber 124 is thereafter to be connected to the chambers 120 in order to accommodate the reagents from these. The reagents and the sample are subsequently to be mixed in the mixing chamber 124. The processes in the chambers 126, 132 and 136 are also to take place in a similar way.

FIGS. 2A-2G show in perspective various structural parts of the cartridge 100 from FIG. 1. An adjustment device 300 in particular (see FIG. 3A) which comprises the actuator 139 and which makes it possible to control the abovementioned processes will be explained below by means of FIGS. 2A-2G.

Figure 2A:
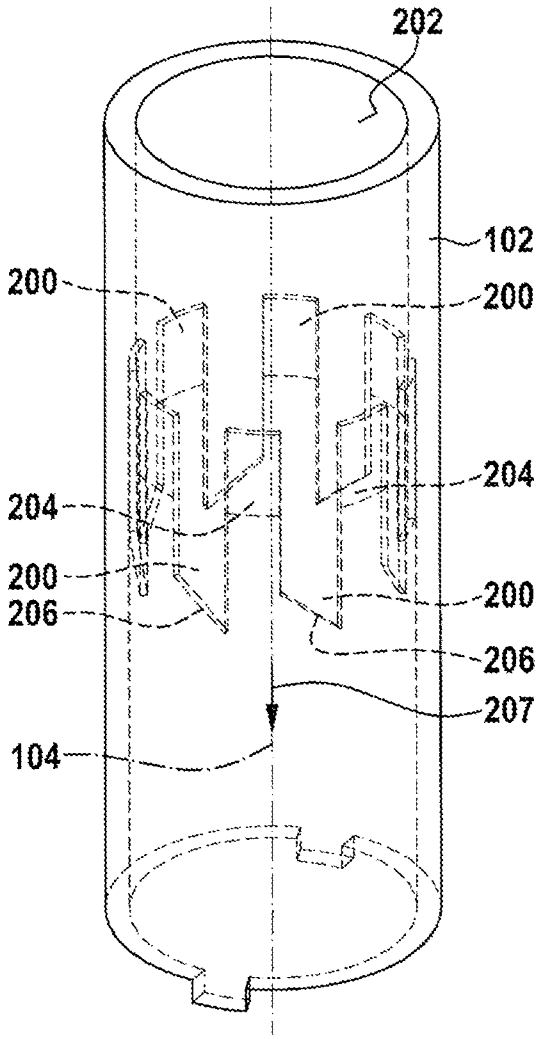
FIGS. 2A-2G show perspective views of various structural parts of the cartridge from FIG. 1.

As shown in FIG. 2A, the housing 102 has on its inside projections 200. The projections 200 project radially with respect to the longitudinal axis 104 from the housing inner wall 202. The projections 200 form between them slots 204 which extend along the longitudinal axis 104. The projections 200 are formed in each case at one end with a slope 206. The slopes 206 point in a first direction 207. According to the present exemplary embodiment, they point in the direction of the end 112 of the housing 102.

Figure 2B:
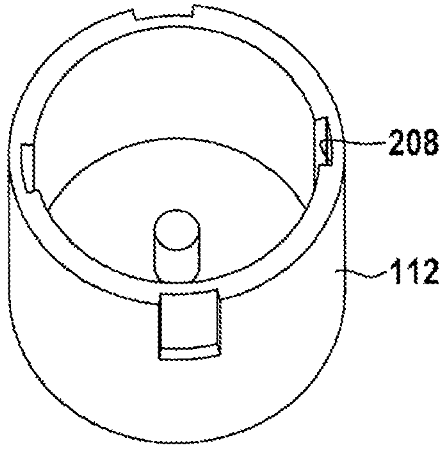

FIG. 2B shows that end 112 of the housing 102 which, according to this exemplary embodiment, is designed as a removable cap. The end 112 has on its inner circumference a plurality of grooves 208 which extend along the longitudinal axis 104.

Figure 2C:
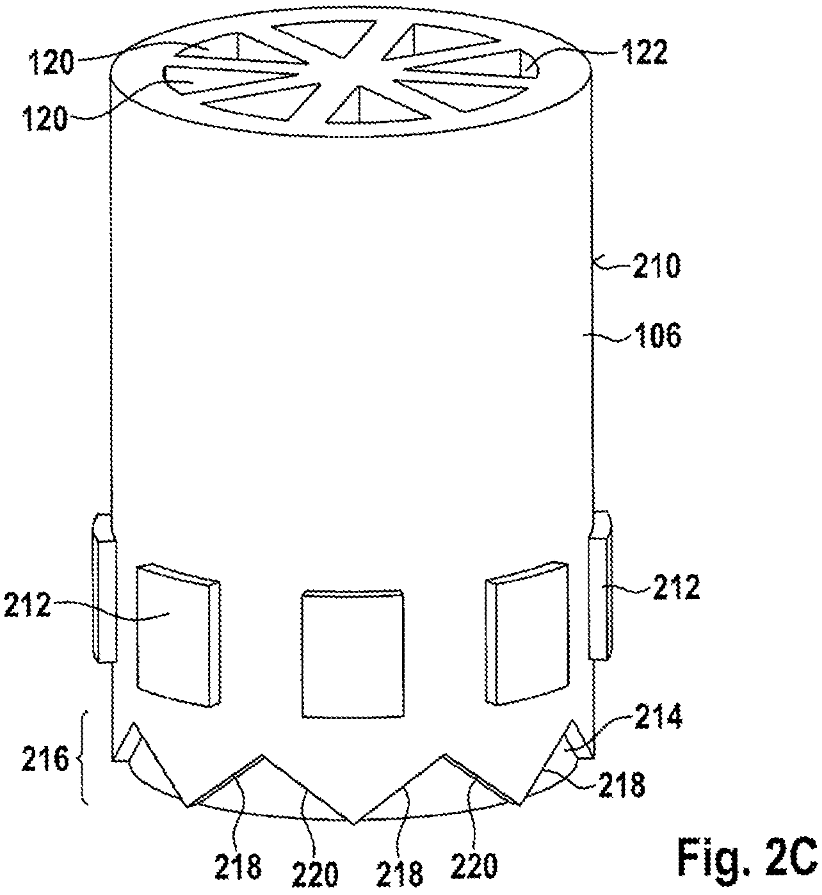

FIG. 2C shows the second drum 106 with the chambers 120, 122. The drum 106 has on its outer wall 210 a plurality of projections 212 which extend radially outward from the outer wall 210. When the cartridge 100 is in the assembled state, the projections 212 of the drum 106 engage into the slots 204 of the housing 102. Rotation of the drum 106 about the longitudinal axis 104 is thereby blocked. However, the drum 106 is displaceable along the longitudinal axis 104 in the slots 204. Furthermore, the second drum 106 has on its outer wall 210, particularly at its end 214 facing the first drum 108, a crown-like contour 216 which comprises a multiplicity of slopes 218, 220. Two slopes 218, 220 form in each case a serration of the crown-like contour 216. The slopes 218, 220 likewise point in the first direction 207.

Figure 2D:
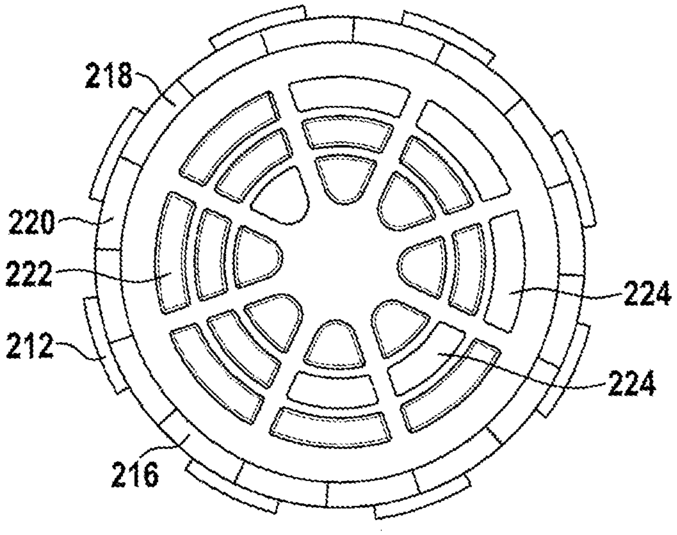

FIG. 2D shows a view of the second drum 106 from FIG. 2C from below. The underside 222, assigned to the end 214, of the second drum 106 has a plurality of orifices 224 in order to connect the chambers 120, 122 to the mixing chamber 124 of the first drum 108 in a liquid-, gas- and/or particle-conducting manner (thereafter "conductively"). Alternatively or additionally, the orifices 224 may also connect the chambers 120, 122 conductively to the chamber 126 of the first drum 108. A respective conductive connection is governed by the position of a respective orifice 224 with respect to the chambers 124, 126. This position is achieved by rotating the first drum 108 with respect to the second drum 106, as is explained in yet more detail later.

Figure 2E:
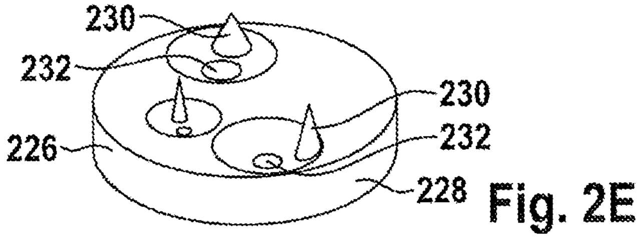

FIG. 2E shows a lancet device 226 which is not illustrated in FIG. 1. The lancet device 226 comprises a plate 228 with one or more spikes 230 which are arranged in each case adjacently to an orifice 232 in the plate 228. The spikes 230 serve, by means of suitable control by the actuator 139, for piercing a respective orifice 224 in the underside 222 of the second drum 106, whereupon, in particular, liquid flows out of the corresponding chamber 120, 122 through the orifice 232 into the chambers 124 or 126.

Figure 2F:
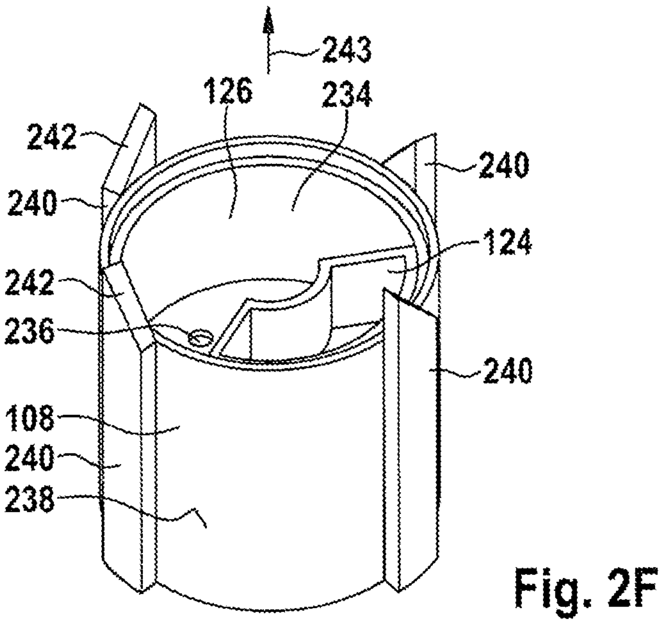

FIG. 2F shows the first drum 108 with the chambers 124, 126. On the bottom 234 of the chamber 126, for example, an orifice 236 is provided for a conductive connection of the chamber 126 to the chambers 132, 136 of the third drum 110. The first drum 108 has on its outer wall 238 a plurality of projections 240. The projections 240 are arranged so as to engage into the slots 204 (exactly like the projections 212 of the second drum 106). As long as the projections 240 are in engagement with the slots 240, rotation of the first drum 108 about the longitudinal axis 104 is blocked. However, the projections 240, together with the first drum 108, are movable along the longitudinal axis 104 in the slots 204. The projections 240 have slopes 242 which point in a second direction 243 opposite to the first direction and which are formed so as to match with the slopes 206 and 220. According to the present exemplary embodiment, the second direction 243 points in the direction of the closure 118.

Figure 2G:
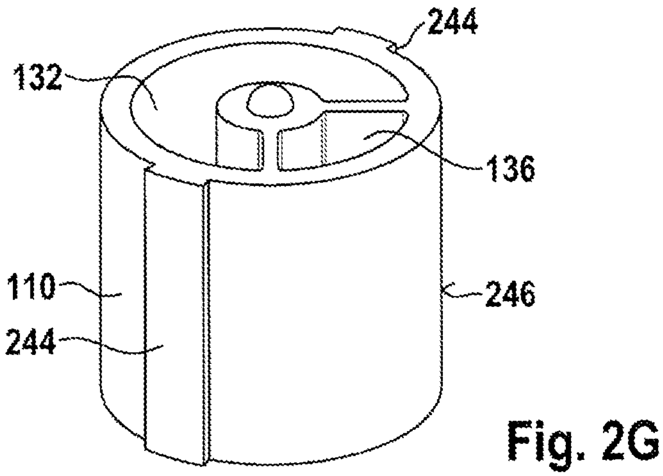

FIG. 2G shows the third drum 110 with the chambers 132, 136. The drum 110 has projections 244 which project in each case from the outer wall 246 of the drum 110. The projections 244 are arranged so as to engage into the grooves 208 at the end 112, so that the drum 110 is displaceable in the longitudinal direction 104 in the grooves 208. However, rotation of the drum 110 about the longitudinal axis 104 is thus blocked.

Figure 3A:
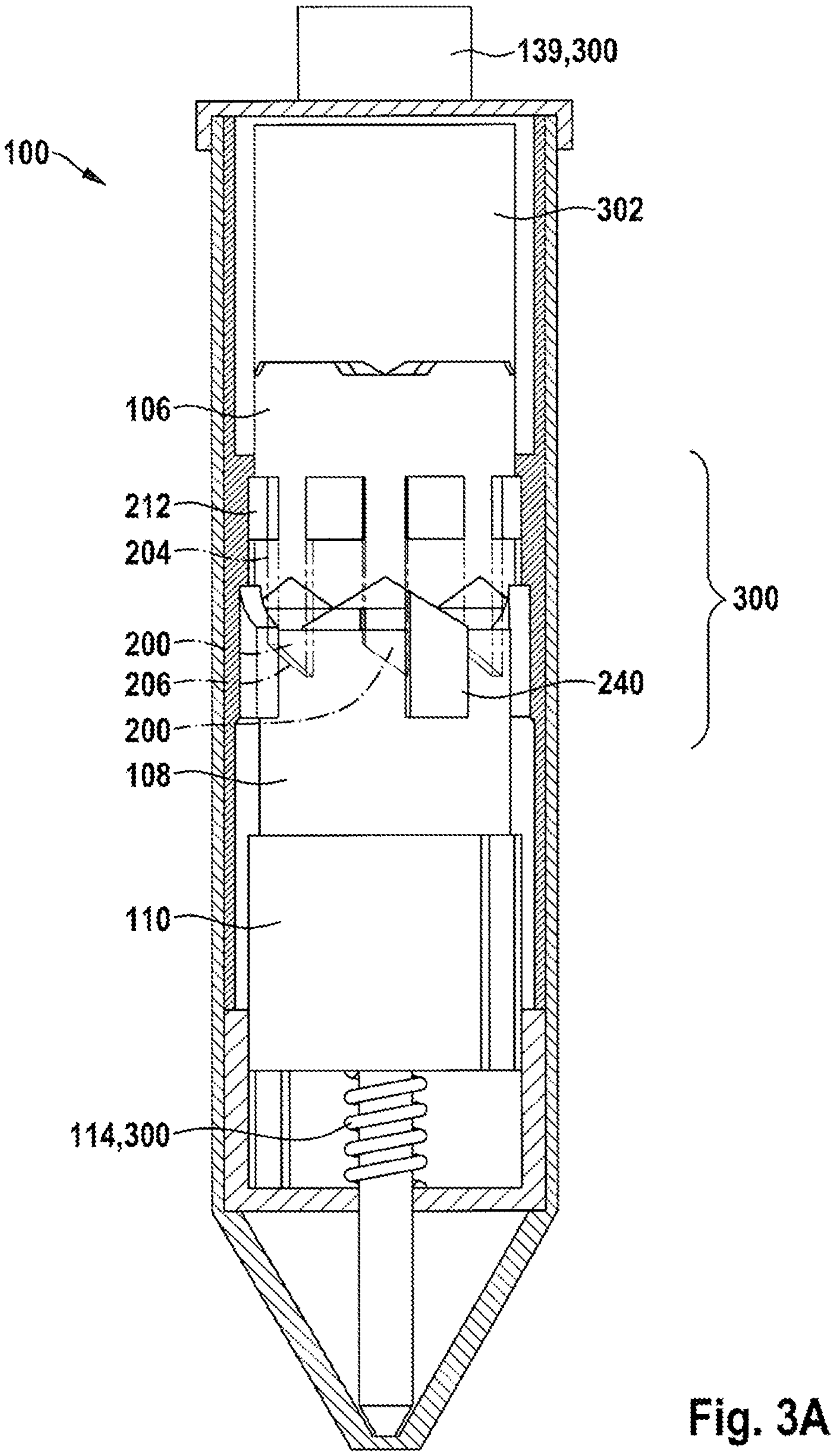
FIGS. 3A-3E show various operating states of the cartridge from FIG. 1.
Figure 3B:
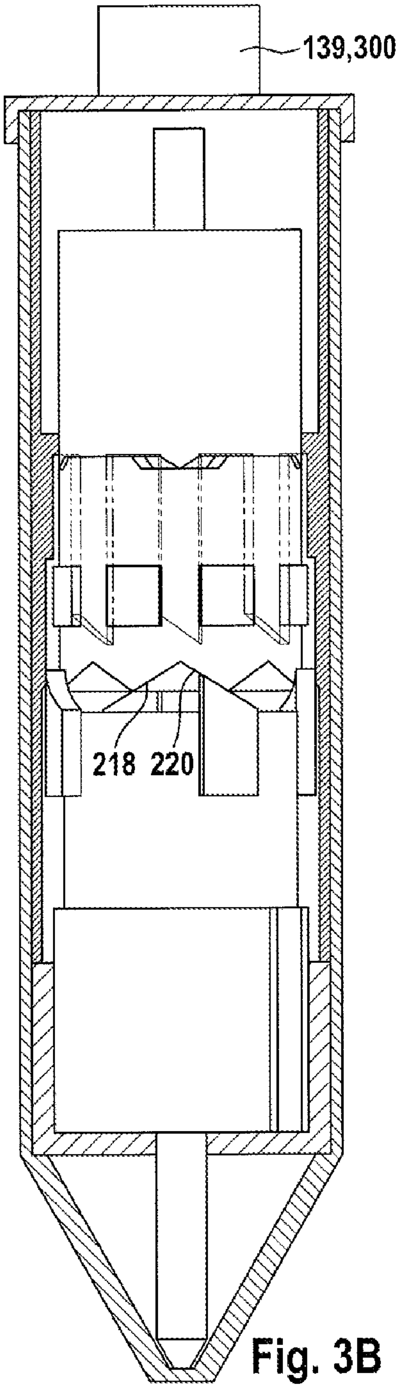
Figure 3C:
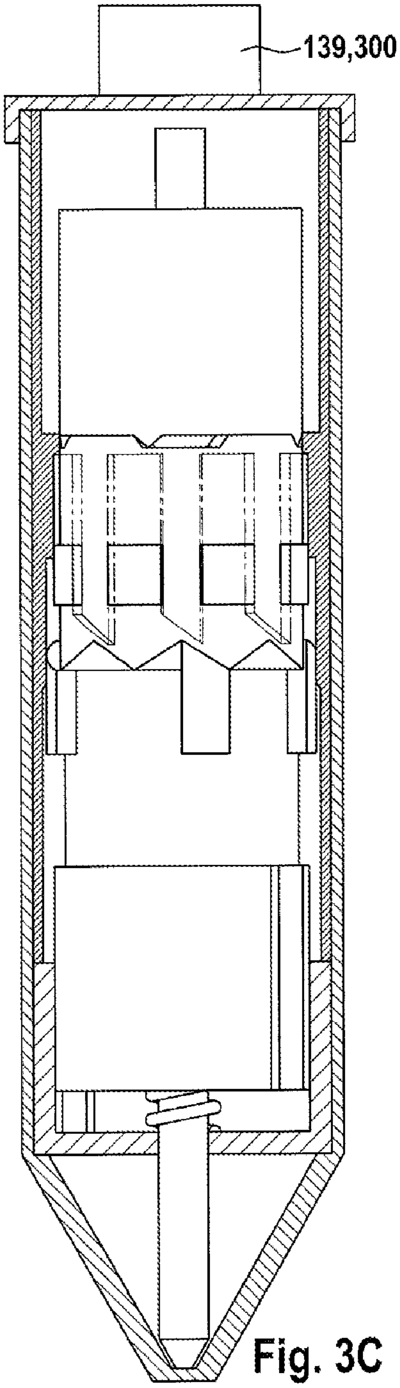
Figure 3D:
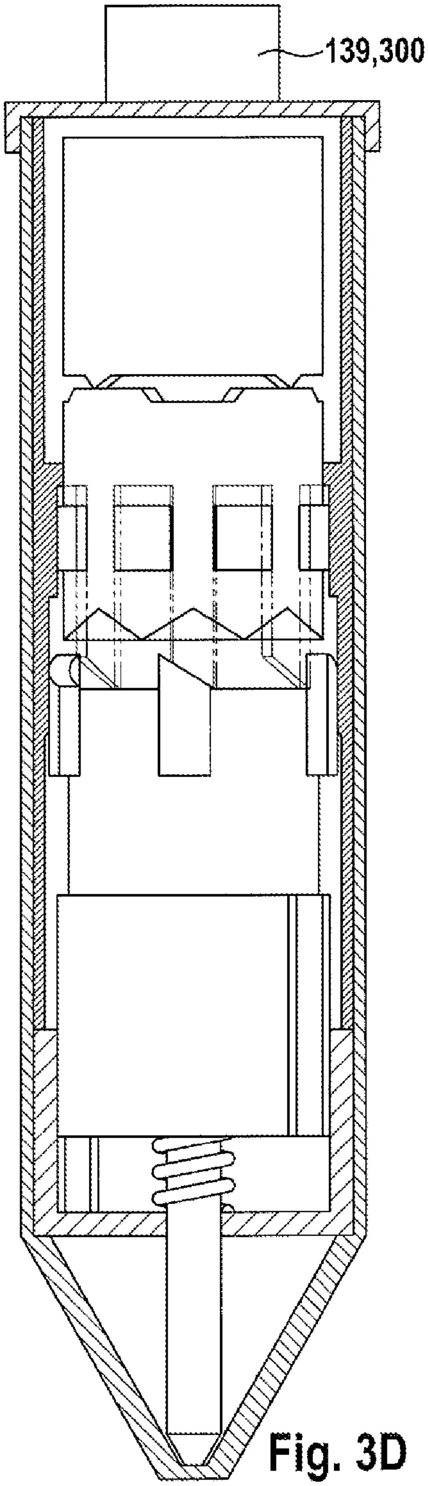
Figure 3E:
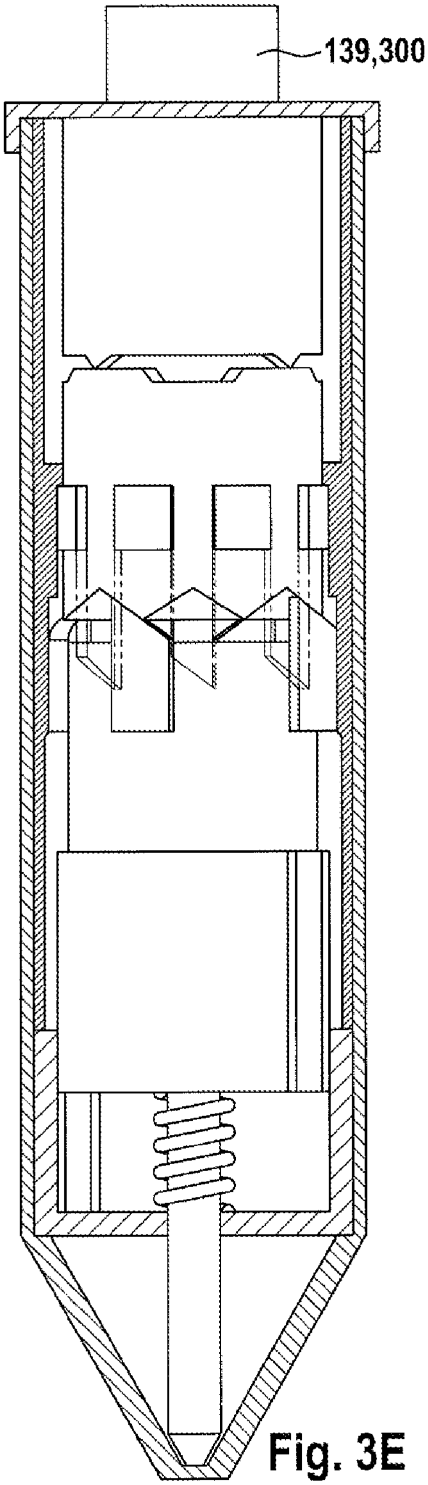

FIGS. 3A-3E show several operating states during the operation of the cartridge 100 from FIG. 1, with an additional drum 302 being illustrated, although this is not relevant any further in the present context. FIGS. 4A-4E correspond in each case to FIGS. 3A-3E and illustrate the movement of the slopes 206, 218, 220, 242 in relation to one another. It may additionally be pointed out, however, that FIG. 3B shows an operating state of the cartridge 100 which is more advanced than the state shown in FIG. 4B. In FIGS. 3A-3E, the housing 102 is illustrated as being partially transparent in order to give a view of the interior.

The actuator 139, projections 200, slots 204, slopes 206, projections 212, slopes 218, 220, projections 240 and slopes 242 form, in the integration with the restoring spring 114, the abovementioned adjustment device 300 for the defined rotation of the first drum 108 with respect to the other drums 106, 110 about the longitudinal axis 104.

Figure 4A:
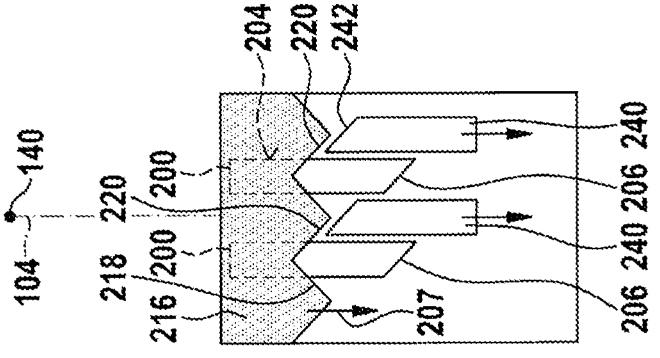
FIGS. 4A-4E show detail views of an adjustment device correspondingly to the various operating states from FIGS. 3A-3E.
Figure 4B:
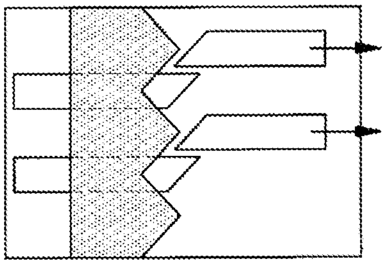
Figure 4C:
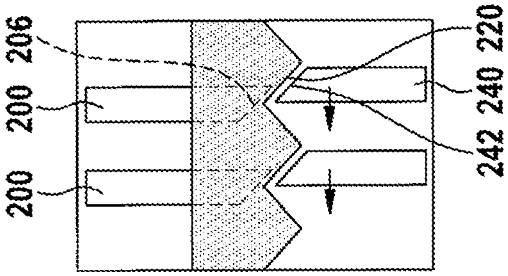

FIGS. 3A and 4A show a first position in which the projections 240 of the first drum 108 engage into the slots 204 and rotation of the first drum 108 about the longitudinal axis 104 is thus blocked. If, then, the actuator 139 presses indirectly or directly upon the second drum 106, the second drum 106 in turn presses, by means of the slopes 220 of the contour 216, onto the slopes 242 of the first drum 108 counter to the action of the spring 114, the spring 114 being compressed. As a result, the first drum 108 moves in the first direction 207, as indicated by the corresponding arrows in FIGS. 4A and 4B. This movement is continued until the projections 240 come out of engagement with the projections 200. In this second position, rotation of the first drum 108 about the longitudinal axis 104 is enabled, as illustrated in FIG. 4C. On account of the cooperation of the slopes 220 and 242 which, for example, are oriented in each case at an angle of 45° with respect to the longitudinal axis 104, a force component is obtained which automatically rotates the first drum 108 if the latter assumes the second position, as indicated by arrows directed to the left in FIG. 4C.

If the actuator 139 then releases the second drum 106, the spring 114 displaces the first drum 108 in the second direction 243 again by means of the third drum 110. As a result, the second drum 106, together with its slopes 220, is likewise moved in the second direction 243 again, with the result that the slopes 242 of the first drum 108 come to lie against the slopes 206 of the housing 102 and slide along these, while at the same time a further rotational movement of the first drum

Figure 4D:
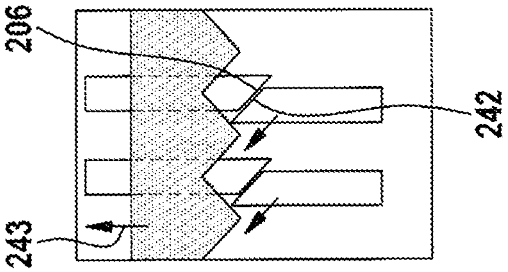
Figure 4E:
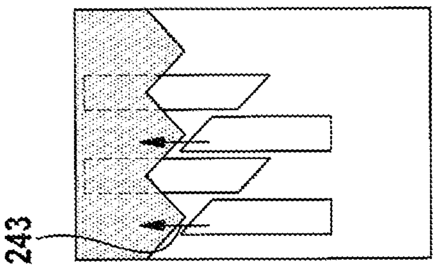

108 into a third position takes place, as illustrated in FIGS. 4D and 4E. In the third position, the projections 240 of the first drum 108 are arranged in the slots 204 of the housing 102 again, so that further rotation of the first drum 108 about the longitudinal axis 104 is blocked again.

The process described above may be repeated as often as desired in order to rotate the first drum 108 in a defined manner with respect to the other drums 106 and 110.

Instead of the actuator 139, a centrifuge could be used, as before. For this purpose, the cartridge 100 may have an external geometry such that it can be inserted into a receptacle of a rotor of the centrifuge, in particular into a receptacle of an oscillating rotor or fixed-angle rotor of a centrifuge. During centrifuging, the cartridge 100 is rotated at a high rotational speed about a center of rotation 140 indicated diagrammatically in FIG. 1. The center of rotation 140 lies in this case on a longitudinal axis 104, so that a corresponding centrifugal force 142 acts along the longitudinal axis 104 upon each constituent of the cartridge 100. By means of a suitable control of the rotational speed, various processes within the cartridge 100 can be controlled, as when the actuator 139 is used.

As a further alternative, a further actuator, not illustrated, could also be used instead of the restoring means 114.

Basically, the actuator 139 may be electrically operated, mechanically operated and/or pressure operated. In particular, a piezoelectrically, electrostatically, semi-mechanically/manually or electromagnetically operated actuator 139 is appropriate. Here, "operating" means the active principle which the actuator 139 utilizes in order to generate the actuation force for actuating the second drum 106 (or, depending on the embodiment, also one of the other drums 108, 110). For example, the actuator 139 may have an electromagnet which cooperates with a metal part which is arranged in one of the drums 106, 108, 110 and which the electromagnet protracts or repels by means of suitable activation of the latter, in order thereby to achieve the above-explained adjustment of the drums 106, 108, 110 with respect to one another. The pressure force applied to the second drum 106 by means of the actuator 139 amounts typically to 0.5-100 N.

A suitable control device, not illustrated, is preferably provided, which activates the actuator 139 so that the drums 106, 108, 110 assume at the desired time the position with respect to one another which is desired in each case. For this purpose, the control device may have a timer and/or an integrated circuit.

According to one refinement, the system 103 may be provided without the projections 200, slots 204, slopes 206, projections 212, slopes 218, 220 and restoring spring 114. Instead, the actuator 139 has a shaft which is connected directly to the first drum 108. The actuator 139 then, as a result of suitable activation by means of the control device, rotates the first drum 108 with respect to the then fixed other drums 106, 110, in order to connect the various chambers, for example the chambers 120, 124, conductively to one another. In order to achieve a suitable movement (a rotational movement about the longitudinal axis 104 and/or a movement along the longitudinal axis 104 in the first and/or the second direction 207, 243) of the drums 106, 108, 110 with respect to one another, two or more actuators 139 may also be used.

Figure 5:
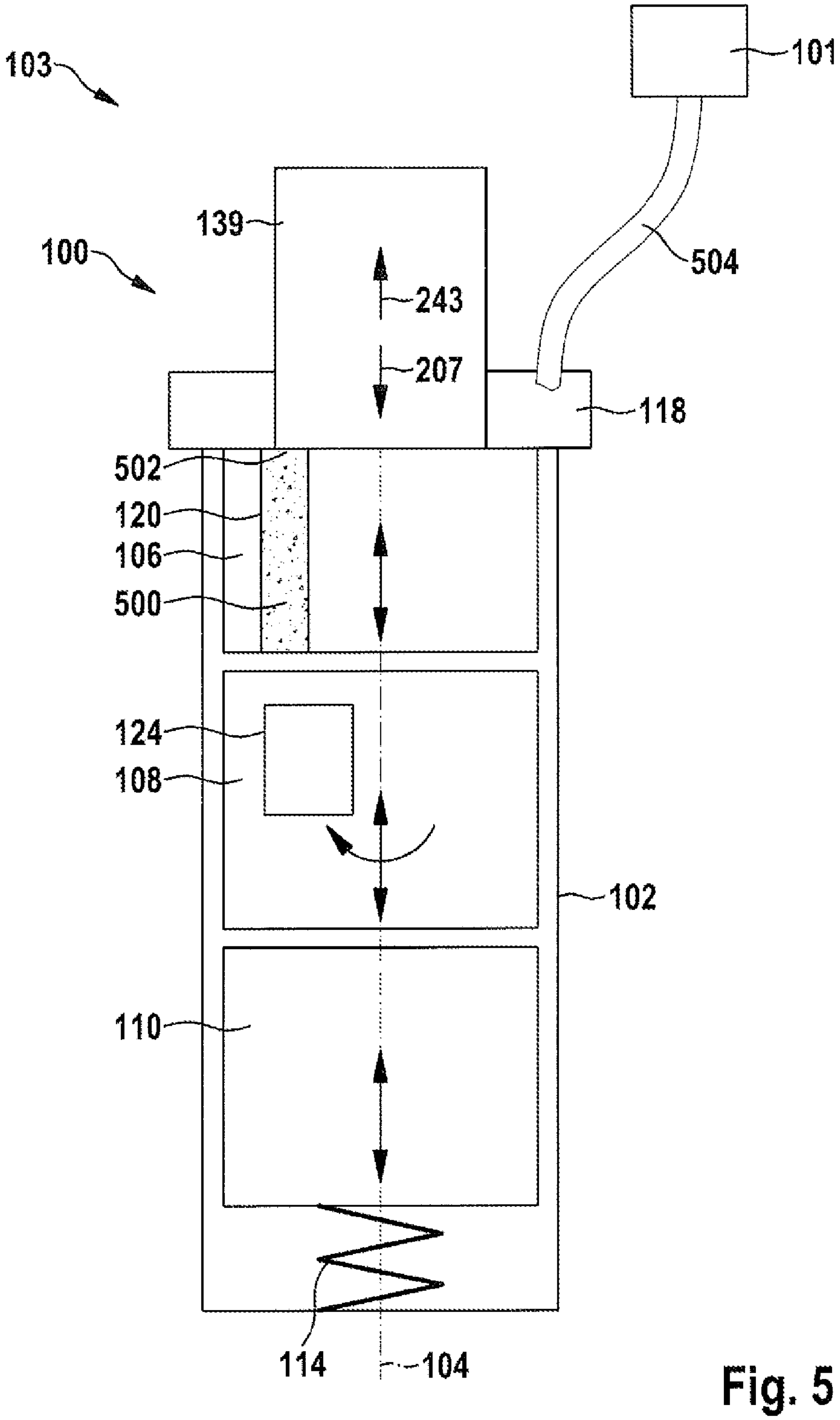
FIG. 5 shows diagrammatically a sectional view of a system comprising an actuator which passes through an adapter, according to a further exemplary embodiment of the present disclosure.

FIG. 5 shows diagrammatically a sectional view of a system 103 according to a further exemplary embodiment of the present disclosure.

In this exemplary embodiment, the cover 118 is designed in the form of an adapter for holding the actuator 139. The actuator 139 extends through the adapter 118 and thus engages directly on the second drum 106 in order to move the latter in the first direction 207, that is to say downward in FIG. 5. For example, for this purpose, the actuator 139 may have an actuating member, in particular a rod, which presses against the drum 106. Return may take place, as described above, by means of the restoring means 114.

Alternatively, the actuator 139, for example the actuating member, is connected fixedly to the second drum 106. The drum 106 can thereby be moved quickly back and forth along the longitudinal direction 104 by means of the actuator 139, with the result that a mixing chamber for mixing components could be provided in one of the chambers 120, 122. If the selected amplitude of the back-and-forth movement is sufficiently low, this movement can take place without the drums 106, 108, 110 being rotated with respect to one another, that is to say the "ballpoint pen mechanism" is not triggered.

The pressure device 101 has the function of acting upon at least one component 500, in particular a liquid, for example a reagent, with a pressure difference, in order to transfer it, for example, out of the chamber 120 into the chamber 124. For this purpose, the chambers 120, 124 are first arranged opposite one another (by the rotation of the first drum 108, as described above) and are thereafter connected, pressure-tight, to one another. Moreover, the second drum 106 seals off with respect to the adapter 118, so that a corresponding pressure-carrying duct in the adapter 118 is connected, pressure-tight, to the chamber 120. The pressure device 101 then, for example, applies a pressure which is above the ambient pressure to the adapter-side end 502 of the chamber 120. The chamber 124 is, for example, bled toward the surroundings, so that the pressure drives the component into the chamber 124. Alternatively, the chamber 124 may in turn be connected conductively to further chambers 126, 132, 136 (see FIG. 1) in the first drum 108 and/or in the third drum 110, only the last chamber 136 being bled, so that the pressure drives the component 500 or else a mixture of the component 500 with further components or only a constituent of the component 500 through the chambers 124, 132, 136. The pressure device 101 typically generates a pressure of 0.01-2 bar.

Alternatively, the pressure device 101 may also be provided for supplying the pressure difference by means of generation of a vacuum.

The pressure device 101 is designed, for example, as a pump. For example, it may be a hand-operated or electrically operated pump.

Alternatively, the pressure device 101 may be designed as a pressure accumulator. The pressure accumulator 101 may be designed, for example, as a spring accumulator which initially contains the component 500 itself and, particularly as a result of the actuation of a valve, conveys the component 500 through the chamber 120 into the chamber 124. Furthermore, there is the possibility that the pressure device 101 stores a fluidic aid under pressure. In particular, compressed air may be considered as an aid. When the air expands, it drives the component 500, in particular a liquid, out of the chamber 120 into the chamber 124 or through a multiplicity of chambers, as described above.

The pressure device 101 is provided, in particular, outside the cartridge 100 and is connected, for example, by means of a pressure connection 504 to the cartridge 100, in particular the adapter 118. Alternatively, the pressure device 101, particularly in the form of a compressed gas accumulator, could also be integrated into the cartridge 100, in particular into one of the chambers 120, 122, 124, 126, 132, 136.

Figure 6:
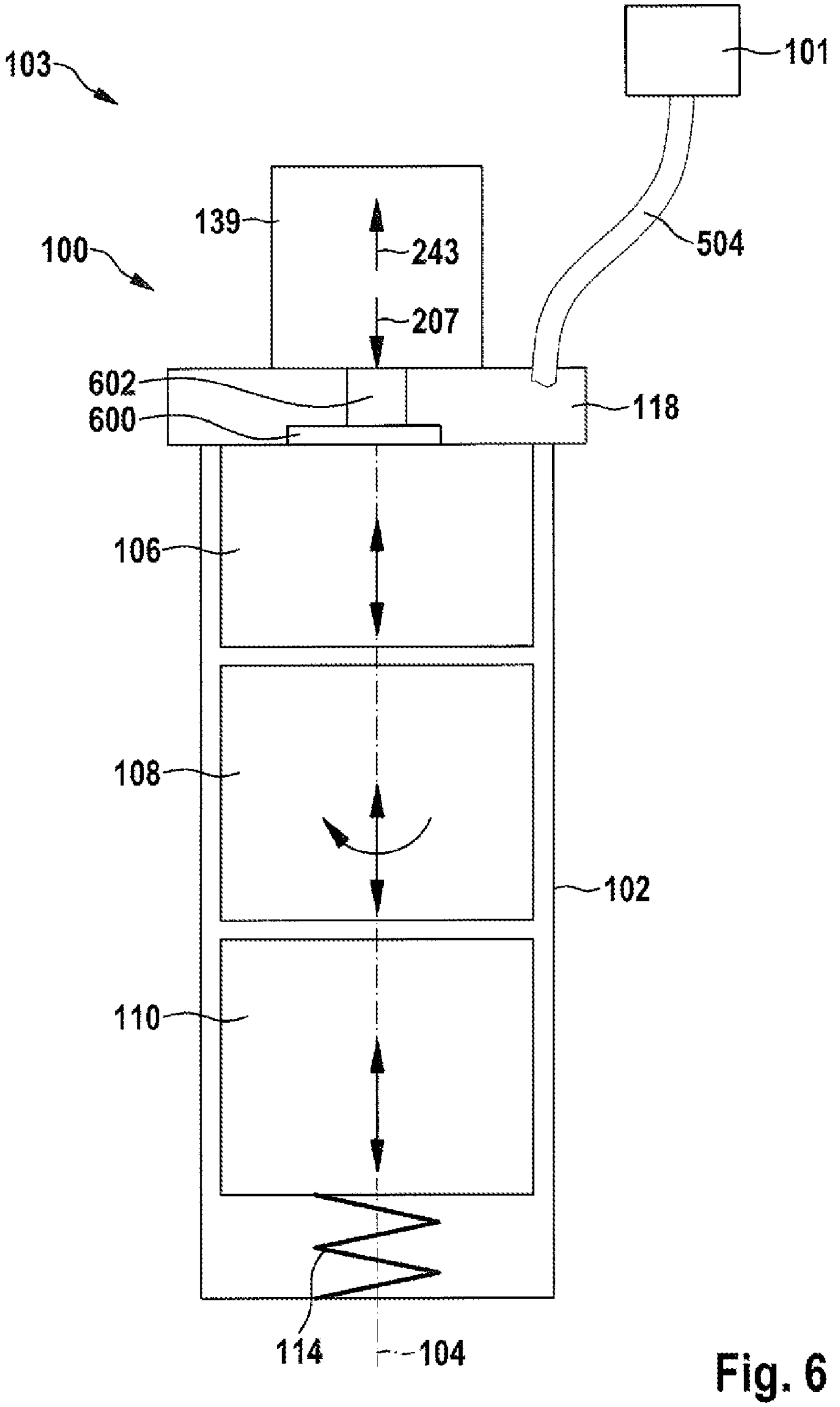
FIG. 6 shows diagrammatically a sectional view of a system comprising an actuator which is arranged on an adapter on the outside, according to yet a further exemplary embodiment of the present disclosure.

FIG. 6 shows diagrammatically a sectional view of a system 103 according to yet a further exemplary embodiment of the present disclosure.

The exemplary embodiment according to FIG. 6 differs from that according to FIG. 5 in that the actuator 139 is attached to the adapter 118 on the outside, that is to say, in this case, the actuator 139 does not pass through the adapter 118. Instead, the actuator 139 acts indirectly, specifically, for example, by means of a flexible diaphragm, upon the second drum 106 in order to actuate the latter in the first direction 207. In particular, a thin portion 600 of the adapter 118 forms the diaphragm, an actuating member 602 of the actuator 139 deforming this thin portion 600 elastically.

Figure 7:
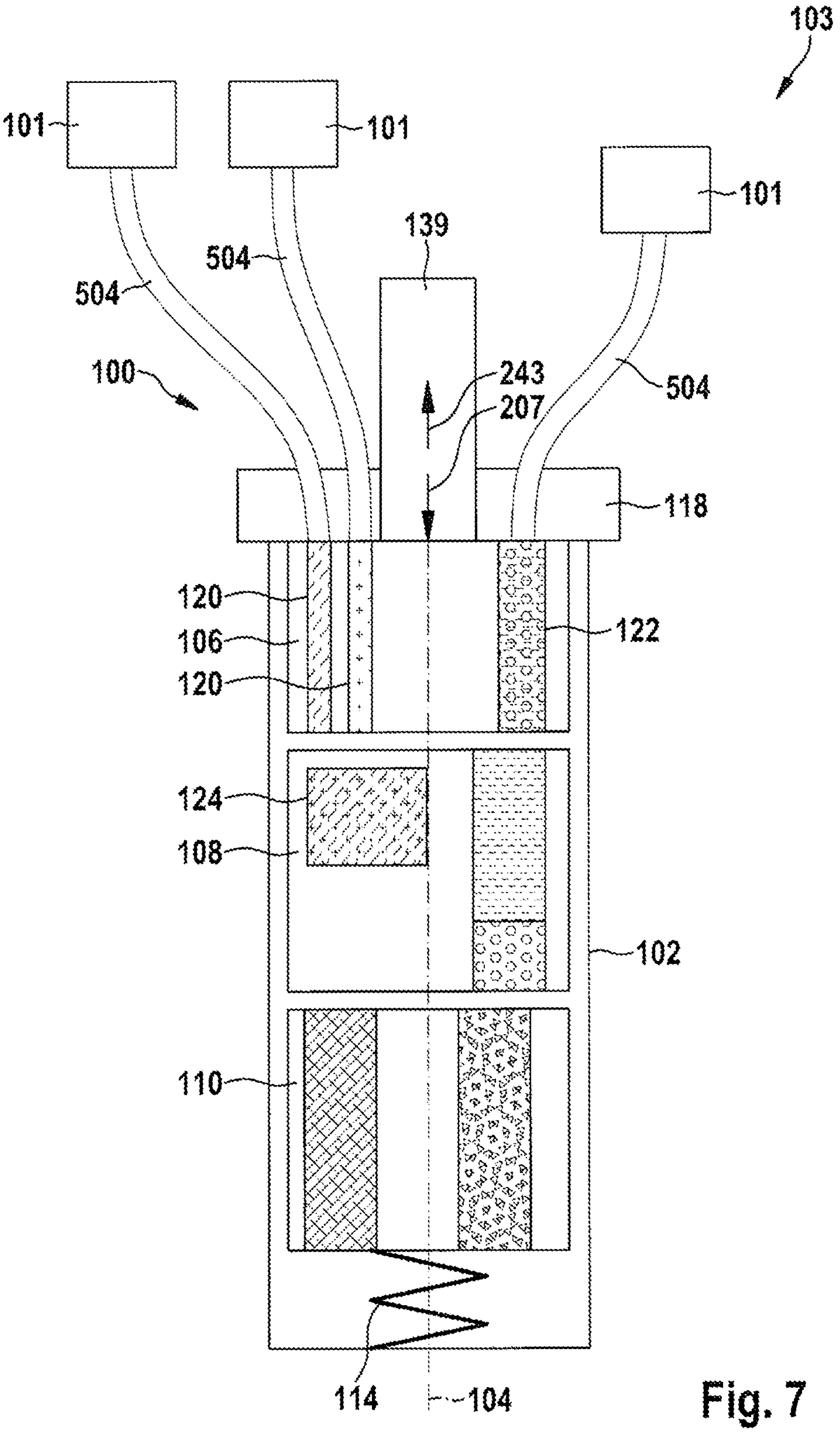
FIG. 7 shows diagrammatically a sectional view of a system comprising a plurality of pressure connections according to yet a further exemplary embodiment of the present disclosure.

FIG. 7 shows diagrammatically a sectional view of a system 103 according to yet a further exemplary embodiment of the present disclosure.

The exemplary embodiment according to FIG. 7 differs from that according to FIG. 5 in that a respective chamber 120, 122 of the second drum 106 is connected to a respective pressure device 101 by means of a pressure connection 504 assigned in each case. The pressures prevailing at the chambers 120, 122 can thereby be controlled individually.

In one embodiment, the adapter 118 possesses a plug device (not illustrated), with the result that, for example, the housing 102, the second drum 106 and/or the chambers 120, 122 are contacted and sealed off. The plug device may have pins (not illustrated) which engage from above into the chambers 120, 122 or other orifices of the drum 106 and close the latter in a pressure-tight manner. During plugging together, the pins may also open the, for example, previously closed chambers 120, 122 or other orifices, in particular may pierce a covering film. A duct which is connected to a pressure connection 504 and issues into an assigned chamber 120, 122 may run in turn in a respective pin itself.

Figure 8:
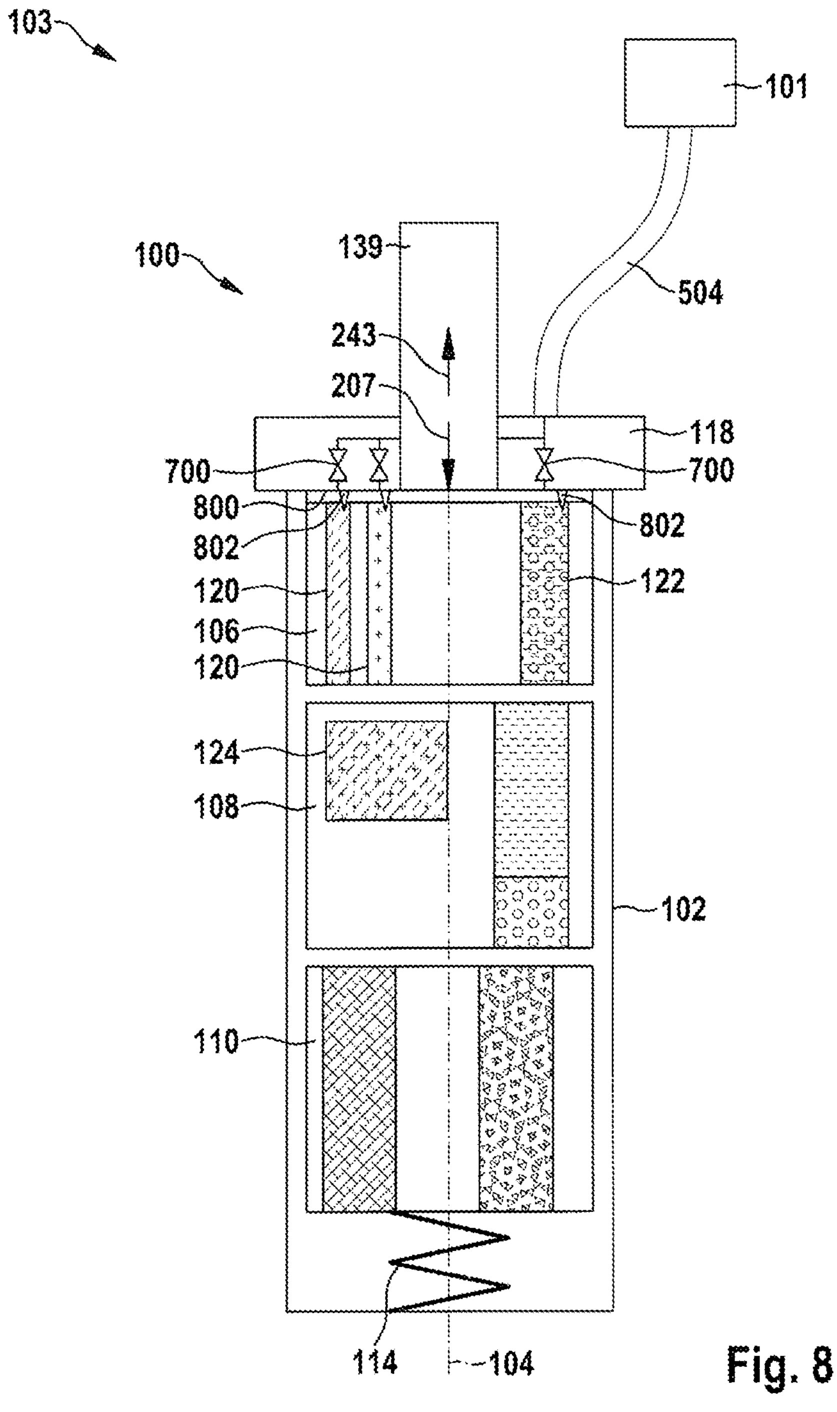
FIG. 8 shows diagrammatically a sectional view of a system comprising a pressure connection and a plurality of valves according to yet a further exemplary embodiment of the present disclosure.

FIG. 8 shows diagrammatically a sectional view of a system 103 according to yet a further exemplary embodiment of the present disclosure.

The exemplary embodiment according to FIG. 8 differs from that according to FIG. 7 in that a respective chamber 120, 122 in the second drum 106 is connected to a single pressure connection 504 by means of a valve 700. The valves 700 may be integrated into the adapter 118.

Moreover, FIG. 8 shows by way of example that one or more spikes 802 may be provided on the inside 800 (that is to say, facing the inner space of the housing 102). Before the action of the pressure by means of the pressure device 101, the actuator 139 first actuates the second drum 106 in the second direction 243 in order thereby to pierce a covering film (not illustrated), for example made from aluminum, which closes a respective chamber 120, 122. Before the piercing step, the drums 106, 108, 110 are rotated suitably in relation to one another, as explained above.

Alternatively, the spikes 802 may also be provided so as to be extendable. Piercing of a respective covering film is then consequently possible independently of actuation by the actuator 139.

Furthermore, there is the possibility of providing the actuator 139 so as to be pressure-operated, for which purpose the actuator 139 is connected (not illustrated) in a pressure-conducting manner to the pressure device 101 and is thus driven by the latter. In the simplest case, the adapter 118 and the second drum 106 form with one another a chamber (not illustrated) which is acted upon with pressure by the pressure device 101, the actuator 139 thus being formed. Furthermore, the actuator 139 could be provided in the form of a concertina which is provided between the adapter 118 and the second drum 106.

The actuator 139 may also be provided elsewhere, for example between the first drum 108 and the second or the third drum 106, 110.

In the simplest case, the actuator 139 may even be omitted, in which case the rotation of the drums 106, 108, 110 in relation to one another takes place manually, in particular by triggering the ballpoint pen mechanism.

A control unit, not illustrated, regulates the interaction of the actuator 139, which predetermines the spatial position of the drums 106, 108, 110, and of the pressure device 101, which controls the pressure for controlling the component 500 (or a plurality of components).

Furthermore, the drums 106, 108, 110 or the chambers 120, 122, 124, 132, 136 may be designed such that further process steps and structures can be integrated, for example sedimentation structures, mixed structures and duct or siphon structures for conducting and switching the liquids.

The housing 102 and the drums 106, 108, 110 may be produced from the same or different polymers. The one or the plurality of polymers may be, in particular, thermoplastics, elastomers or thermoplastic elastomers. Examples are cycloolefin polymer (COP), cycloolefin copolymer (COC), polycarbonates (PC), polyamides (PA), polyurethanes (PU), polypropylene (PP), polyethylene terephthalate (PET) or poly(methyl methacrylate) (PMMA).

One or both of the drums 106, 110 may be formed in one piece with the housing 102.

Although the disclosure was described in the present context by means of preferred exemplary embodiments, it is in no way restricted to these, but can be modified in many different ways. In particular, it should be pointed out that refinements and exemplary embodiments described in the present context for the system according to the disclosure can be applied correspondingly to the method according to the disclosure, and vice versa. Furthermore, it is pointed out that, in the present context, “one” does not rule out a multiplicity.

What is claimed is:

1. A microfluidic system, comprising:

a cartridge defining a longitudinal axis and including:

a first drum which has a first chamber, the first drum defining a first mid-axis, the first drum being arranged with the first mid-axis arranged coaxially with the longitudinal axis, a second drum which has a second chamber, the second drum defining a second mid-axis, the second drum being arranged with the second mid-axis arranged coaxially with the longitudinal axis and preceding or following the first drum with respect to the longitudinal axis, and an adjustment device which is configured to rotate the first drum about the longitudinal axis and, the first drum and the second drum being configured such that the first chamber and the second chamber are connected in one or more of a fluid-conducting manner, a gas-conducting manner, and a particle-conducting manner in response to the first drum being rotated about the longitudinal axis by the adjustment device, and a pressure device coupled to the first chamber and configured to act upon at least one component in the first chamber with a pressure difference and is configured to transfer the component between the first chamber and second chamber.

2. The system according to claim 1, wherein the pressure device is configured to be one or more of a pump and a pressure accumulator, the one or more of the pump and the pressure accumulator being connected by a pressure connection to the cartridge or being integrated into the cartridge.

3. The system according to claim 2, wherein the pressure accumulator stores the component and supplies the component to the first chamber or the second chamber under a pressure of the component.

4. The system according to claim 2, wherein the cartridge has a housing which is closed at an end of the housing by an adapter, the adapter having the pressure connection.

5. The system according to claim 1, wherein the adjustment device includes one or more of an electrically operated, a mechanically operated, and a pressure-operated actuator which rotates the first drum along the longitudinal axis and moves the first drum axially along the longitudinal axis.

6. The system according to claim 5, wherein the actuator has a shaft which is connected directly or indirectly to the first drum and is configured to rotate the first drum.

7. The system according to claim 5, wherein the adjustment device includes a first slope which cooperates with a second slope of the first drum and is configured to bring the first drum out of a first position, in which the first drum is in positive engagement with a housing of the cartridge in a direction of rotation about the longitudinal axis, into a second position along the first mid-axis, in which the positive connection is cancelled and the first drum rotates about the longitudinal axis by virtue of the action of a restoring member or of a further actuator.

8. The system according to claim 7, wherein the actuator actuates the first slope to cooperate with the second slope.

9. The system according to claim 5, further comprising a third drum defining a third mid-axis, the third drum being arranged with the third mid-axis coaxial with the longitudinal axis, the actuator being configured to actuate one or more of the second drum and the third drum to rotate the first drum.

10. The system according to claim 5, wherein the cartridge has a housing which is closed at an end of the housing by an adapter, the actuator being fastened to the adapter.

11. The system according to claim 10, wherein the adapter has a flexible diaphragm which can be actuated on a side by the actuator and which acts on another side upon one or more of the first drum, the second drum, and a third drum.

12. The system according to claim 10, further comprising at least one further chamber configured to be acted upon by the pressure device with pressures different in each case from one another, the second chamber and the at least one further chamber being connected by a respective pressure connection in the adapter to the pressure device, or the second chamber and the at least one further chamber being connected by a single pressure connection in the adapter to the pressure device, the second chamber and the at least one further chamber being connected by a respective valve to the single pressure connection.

13. The system according to claim 5, wherein the pressure device drives the actuator.

14. The system according to claim 2, wherein the pressure accumulator stores the component and supplies the component to the first chamber or the second chamber under pressure of a fluidic aid which pressurizes the at least one component.

* * * * *